United States Patent [19]
Tamura et al.

[11] 4,081,674
[45] Mar. 28, 1978

[54] ION MICROPROBE ANALYZER

[75] Inventors: Hifumi Tamura, Hachioji; Tohru Ishitani, Sayama; Tokuro Hirano, Katsuta, all of Japan

[73] Assignee: Hitachi, Ltd., Japan

[21] Appl. No.: 751,986

[22] Filed: Dec. 20, 1976

[30] Foreign Application Priority Data

Jan. 21, 1976 Japan .................................. 51-4928
May 21, 1976 Japan .................................. 51-57806

[51] Int. Cl.² ...................... G01M 27/78; G01M 23/00
[52] U.S. Cl. ................................... 250/251; 250/309; 250/423 R
[58] Field of Search ........................ 250/309, 251, 423

[56] References Cited
U.S. PATENT DOCUMENTS

| | | | |
|---|---|---|---|
| 2,836,750 | 5/1958 | Weimer | 250/423 |
| 3,415,985 | 12/1968 | Castaing et al. | 250/309 |
| 3,660,655 | 5/1972 | Wardell | 250/309 |
| 3,742,275 | 6/1973 | Gutow | 250/423 |
| 3,790,793 | 2/1974 | King | 250/251 |
| 3,889,115 | 6/1975 | Tamura et al. | 250/309 |

Primary Examiner—Harold A. Dixon
Attorney, Agent, or Firm—Craig & Antonelli

[57] ABSTRACT

An ion microprobe analyzer capable of high-precision analyses, and which provides a beam made up of both ions and neutral particles includes an ion beam deflecting means made up of an aperture which is movable between a position on the ion beam optical axis and a position deviating from the optical axis. At least one first deflector is provided which deflects the ion beam towards the point to be occupied by the aperture situated at the deviating position while leaving the path of the neutral particles unaffected, and at least two second deflectors are provided which deflect the ion beam back towards the ion beam optical axis, so that in the vertical direction the ion beam which has passed through the aperture situated at the deviating position is returned to the optical axis. In this way either the ions or the neutral particles may be selected in accordance with the position of the aperture.

20 Claims, 12 Drawing Figures

FIG. 3b  FIG. 3a    FIG. 5b  FIG. 5a
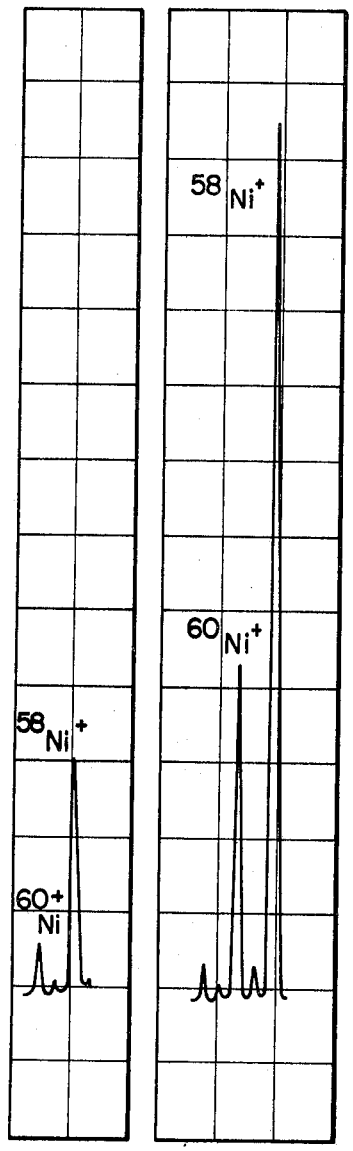
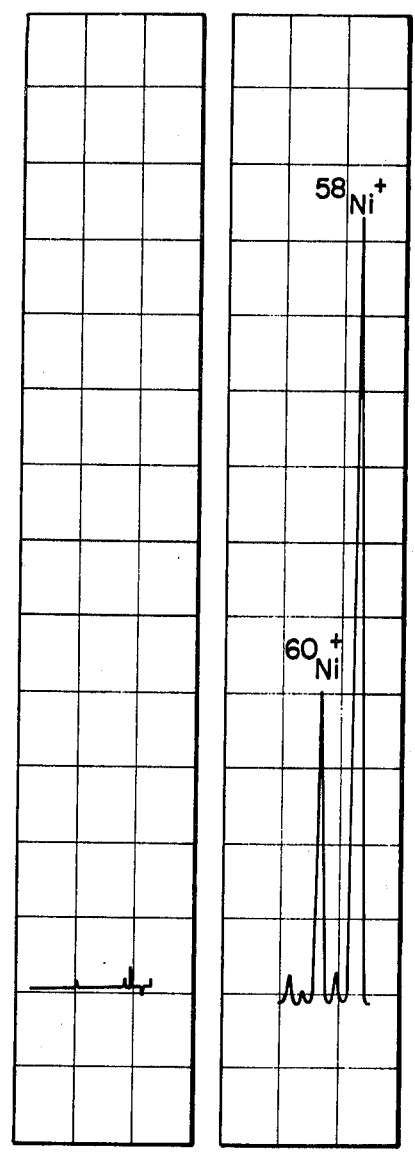

ION MICROPROBE ANALYZER

BACKGROUND OF THE INVENTION

This invention relates to improvements in an ion microprobe analyzer. More particularly, it relates to an ion microprobe analyzer capable of analyses with high precision.

As is well known, the ion microprobe analyzer (hereinafter abbreviated to IMA) is an analytical apparatus for solids and is excellent for microanalysis, in-depth analysis, and surface analysis. An example of a prior art IMA is illustrated in FIG. 1. When broadly separated in function, the IMA is constructed of a primary illumination system, a secondary ion spectrometer and a scanning ion microscope.

The primary illumination system is composed of an ion source 1, condenser lenses 2, object lenses 3, a primary ion scanning deflector 4, an objective aperture 5, a specimen 6, and a shield electrode 7. The function of the primary illumination system is to contract an ion beam 8, generated from the ion source 1, by the two stages of lenses 2 and 3 and to project the ion beam onto the specimen 6. The deflector 4 has the function of scanning the fine contracted beam 8 on the specimen as in a television set. The ion source 1, the two stages of lenses 2 and 3, the objective aperture 5, and the deflector 4 in the primary illumination system are all arranged on one axis.

The secondary ion spectrometer is composed of a secondary ion extractor 9, lenses 10 for correcting the path of a secondary ion beam, an electrostatic sector 11, a $\beta$-slit 12, a magnetic sector 13, a C-slit 14, a secondary detector 15, and a recorder 16 or a counter (not shown). It functions as stated below.

Secondary ions based on specimen atoms as produced from the specimen irradiated by the primary ions are extracted by an electric field which is established by the secondary ion extractor 9. They are led to the electrostatic sector 11, and are subjected to energy separation by the $\beta$-slit 12. Subsequently, the secondary ions having specific energy which have passed through the $\beta$-slit 12 are introduced into the magnetic sector 13 and are sorted on the basis of the mass to charge ratio (M/e), and are detected as specific ion currents by the C-slit 14. The mass spectrum is obtained by gradually varying the field intensity of the magnetic sector 13 with the other conditions fixed. In order to detect the intensity of the secondary ions, a secondary electron multiplier is chiefly utilized.

The scanning ion microscope is composed of a cathode ray tube (hereinbelow, abbreviated to CRT) 17, the operating principle of which with respect to the remaining system is as stated below. First, the finely contracted primary ion beam 8 and the electron beam of the CRT 17 are synchronously scanned by the scanning power supply 31. Subsequently, the image of a specific element or the image of the unevenness of the surface of the specimen is obtained on the CRT 17 by utilizing as the video signal of the CRT 17 a signal obtained by the secondary ion detector 15.

The prior art IMA has inherent problems which will now be discussed, and particularly two contradictory points which are the more significant problems:

i. High-speed neutral particles generated in the ion source 1 get onto the specimen and produce secondary ions which result in the generation of noise. When, for example, a duoplasmatron type ion source is employed as the ion source 1, some ions formed within the ion source are neutralized before getting out of the ion source, and hence, high-speed neutral particles are generated. The high-speed neutral particles have a speed substantially equal to that of the ion beam. In the case where the air pressure of the ion source is $10^{-1}$ Torr, the neutral particles generated amount to about 25% of the ion beam.

ii. The specimen is irradiated by ions which are charged particles. Therefore, in the case where the specimen is an insulator, or where its surface is covered with a nonconductive thin film, the surface of the specimen accumulates an electrical charge and a good analysis thereof becomes difficult.

The problem concerning the neutral particles will be explained in detail in conjunction with FIGS. 2a and 2b, which illustrate the influence of the neutral particles on the operation of the apparatus. Referring to FIG. 2a, the ion beam 8 can have its diameter on the specimen arbitrarily varied by the lens systems 2 and 3. In contrast, the neutral particles indicated by dotted lines in the figure have no charge and are not subject to the focusing action of the lens systems, and accordingly, they advance from the ion source 1 and get to the specimen through the objective aperture 5. The size of the neutral beam 19 on the specimen changes depending on the size of the objective aperture 5, which is in general, several mm.

Now consider a case where the specimen to be analyzed consists of a nickel mesh, as shown in FIG. 2b. In this case, the secondary ions which enter the mass spectrometer after passing through the extractor 9 are of two kinds: the secondary ions resulting from the excitation of the specimen by the primary ion beam, and those owing to the excitation of the specimen by the neutral particles. Moreover, regarding the latter group of ions, the beam diameter is determined by the size of the objective aperture 5 and is large as compared with the diameter of the primary ion beam. Consequently, even when the primary ion beam 8 is projected between the meshes as shown in FIG. 2b, the secondary ions which are generated from a neutral particle irradiation region 20, indicated by a circle in the figure, come into incidence on the spectrometer, and they are detected as noise.

FIGS. 3a and 3b show examples of analyses by the prior art method. FIG. 3a corresponds to a point of analysis A indicated in FIG. 2b, and illustrates the mass spectrum of nickel. FIG. 3b illustrates a spectrum in the case where the primary ion beam was caused to fall on a point B (in FIG. 2b) between the meshes, i.e., a part at which no nickel existed. Although properly the spectrum of nickel ought not to be detected, the nickel spectrum having an intensity of about $\frac{1}{4}$ of the value on the nickel mesh was obtained, as shown in these figures. It is evident that such nickel spectrum is attributed to the high-speed neutral particles. In this manner, in the analysis of a very small part of the specimen by the IMA, unless the neutral particles are removed, the analytical precision of the apparatus is lowered conspicuously and a high-precision analysis becomes difficult. Further, although no explanation is made here, the lowering of the analytical precision is also apparent in the in-depth analysis.

The problem concerning surface charge formation will now be explained. In the IMA, an ion beam is employed as an exciting source. Therefore, where the specimen is an insulator or its surface is covered with a nonconductive film, the charge accumulation phenomenon occurs. Besides, when charged particles are exploited in the case of executing the analysis of a function device, such as an integrated circuit (IC), the electrical characteristics of the IC change under the influence thereof and the reuse of the IC becomes difficult though the cause is not clear.

Regarding this problem, there has been utilized a method wherein charges on the specimen surface are neutralized by superposingly irradiating the ion beam irradiation portion with a low-speed electron beam. Also, a method has been used wherein the charge accumulation is avoided by employing negative ions as the primary ions. In this case, the secondary electrons serve to neutralize the charges. With either method, however, the charged particles are exploited for the primary beam, and the settlement of the latter problem on the electrical characteristics cannot be expected.

SUMMARY OF THE INVENTION

An object of this invention is to provide an IMA which eliminates neutral particles and prevents them from getting onto a specimen, thereby to make high-precision analyses possible.

Another object of this invention is to provide an IMA in which it is possible in the alternative to prevent a specimen from being irradiated by ions.

Still another object of this invention is to provide an IMA which can use as a primary excitation source either an ion beam for effecting microanalysis or a beam of neutral particles which causes no electrification.

These and other objects are accomplished by disposing ion beam deflecting means composed of an aperture and deflectors between the ion source and the specimen.

The ion beam deflecting means which is used in accordance with this invention is composed of a selectively movable aperture and deflectors. More specifically, the ion beam deflecting means is made up of:

a. an aperture which is movable between a position on the ion beam optical axis and a position deviating from the optical axis;

b. at least one first deflector which deflects the ion beam towards the position of the aperture when situated at the deviating position; and c. at least two second deflectors which deflect the ion beam which has passed through the aperture situated at the deviating position forwards along the ion beam optical axis.

The deflecting means may lie at any position on the ion beam optical axis between the ion source and a specimen. Preferably, however, it is provided between the ion source and the primary ion focusing system.

It is preferable that all of the components of the primary illumination system between the ion source and the specimen are disposed of a single rectilinear axis.

BRIEF DESCRIPTION OF THE DRAWINGS

FIGS. 2a and 2b and FIGS. 3a and 3b are diagrams for explaining problems of the prior art IMA;

FIGS. 5a and 5b are diagrams for explaining an effect of this invention;

Hereunder, this invention will be described in detail in connection with various exemplary embodiments.

Figure 1:
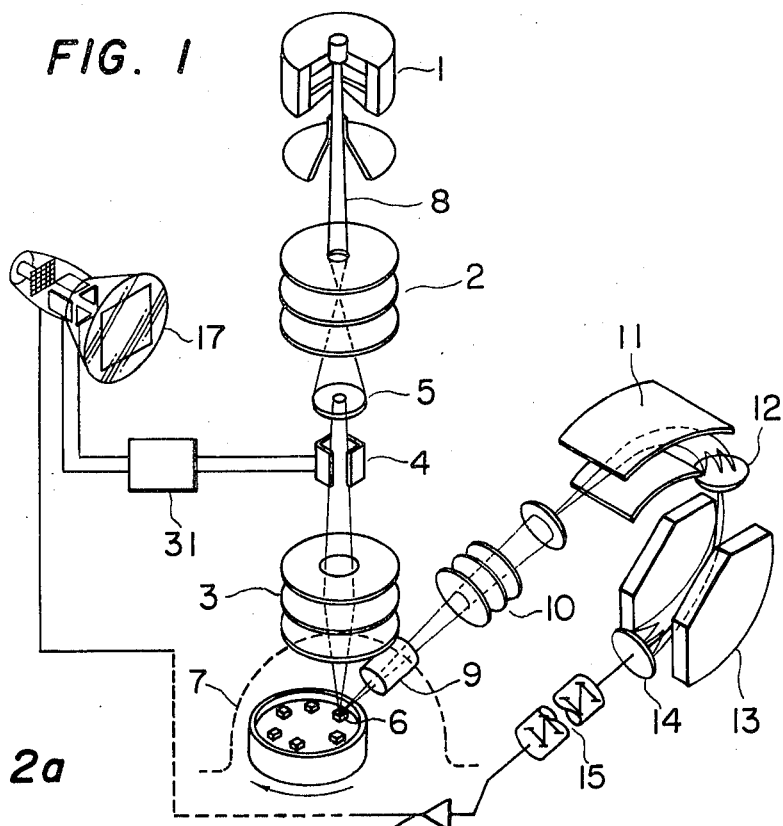
FIG. 1 is a view showing the construction of a prior art IMA.
Figure 2A:
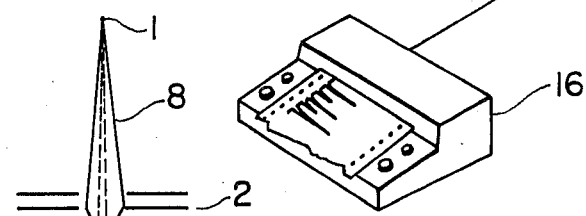
Figure 2B:
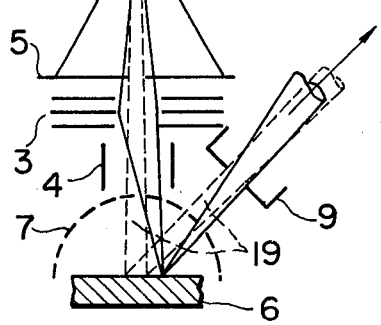
Figure 2B:
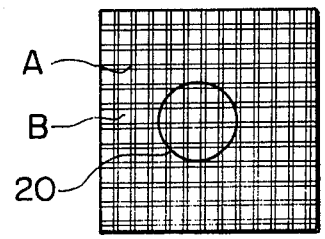
Figure 4B:
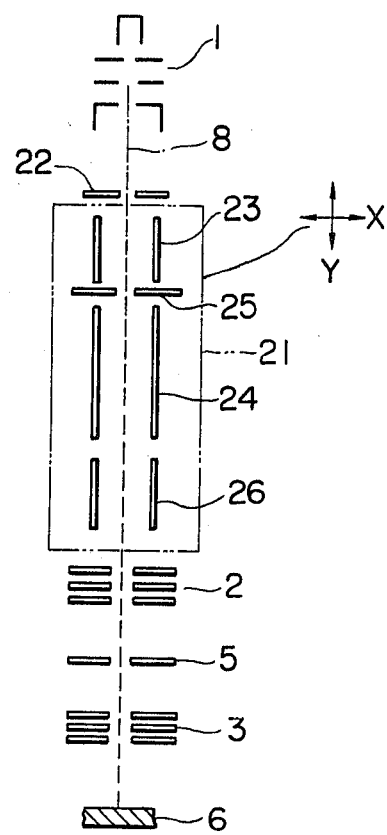
FIGS. 4a and 4b are explanatory views of an embodiment of this invention.
Figure 4A:
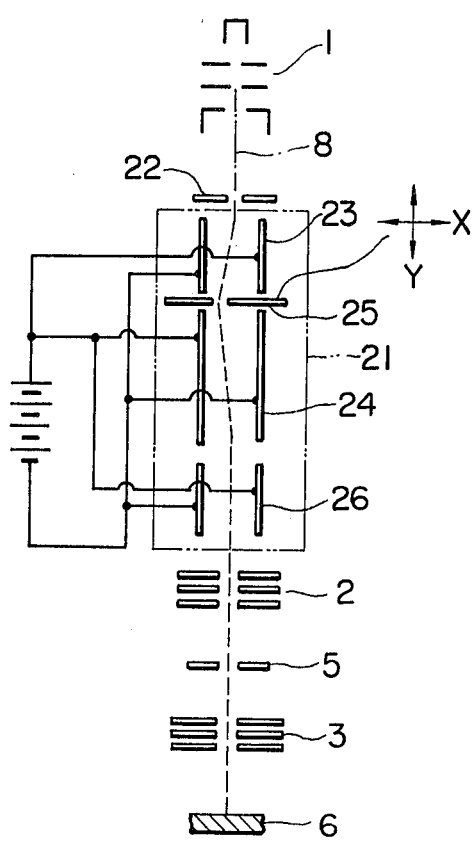

FIGS. 4a and 4b show an embodiment of this invention in which the present invention is exemplified by an apparatus in which both an ion beam and a high-speed particle beam can be utilized as an incident primary particle source of an IMA. The fundamental operating principle of this embodiment is that means 21 for deflecting an ion beam is provided anew between the ion source 1 in the prior art and the primary ion beam focusing system including the condenser lenses 2 and the succeeding components, whereby only the ion beam or the neutral particles are allowed to reach the specimen but not both.

In order to realize this method, two expedients illustrated in FIGS. 4a and 4b are employed. The deflecting means 21 is composed of a first deflector 23, second deflectors 24 and 26, and an aperture 25. Preferable design conditions are that the deflector 23 and the deflector 26 are of the same size and shape and that the deflector 24 is made twice as long as the deflectors 23 or 26. When, as illustrated in FIG. 4a, an identical voltage is applied to the deflectors 23, 24, and 26 thus constructed, the ion beam vertically entering from above emerges vertically at all times after passing through the deflecting system. Of course, even when the shapes of the deflectors are arbitrarily selected, the vertical emergence of the ion beam along the common axis can be realized by applying proper voltages to the respective deflectors.

The aperture 25 intervening between the deflectors 23 and 24 is designed so as to be movable forwards and rearwards within a horizontal plane. The aperture 25 has the following two functions. In the first function, it is arranged in a manner to deviate from the axis of the deflectors as illustrated in FIG. 4a, whereby the neutral particles are intercepted and removed, while the ion beam is deflected through the aperture, as shown by the deflecting system, so as to pass on to the specimen. In the second function, the aperture 25 is arranged on the axis, whereby the neutral beam can reach the surface of the specimen, and simultaneously therewith, a proper voltage is applied to any one of the deflectors 23, 24, and 26, whereby the ion beam is deflected so as to be intercepted, thereby preventing it from reaching the specimen surface. According to such a method, the ion beam and the neutral particles can be independently taken out by moving the aperture 25 interposed between the deflectors 23 and 24. It is preferable that a further aperture 22 is provided between the deflecting means 21 and the ion source 1, but such is not essential.

Description will now be made of another embodiment in which, in independently selecting the ion beam or the neutral beam for the irradiation of the specimen, the deflecting means 21 itself is moved. The principle of this method is illustrated as shown in FIG. 4b. In this case, the whole portion indicated by a dotted line can be moved relative to the ion beam optical axis within a horizontal plane. First, in case of irradiating the specimen by the neutral beam, the axis of the deflecting system and the ion beam optical axis are brought into coincidence, as illustrated in FIG. 4b. The ion beam is deflected from the axis by any one of the deflectors 23, 24, and 26, and is made incapable of reaching the specimen. Thus, an analysis by the neutral particles is carried out.

In case of removing the neutral particles and performing an analysis with the ion beam, the deflecting means 21, enclosed within the dotted line in FIG. 4b, is wholly moved to cause its axis to deviate from the ion beam optical axis. Thus, the neutral particles are removed, and the ion beam is deflected, guided to the lens system and focused on the specimen by a method similar to that illustrated in FIG. 4a.

In this case, the ion beam and the neutral beam are separately used by moving the deflecting means 21, and the effect is the same as in the foregoing case where only the aperture 25 is movable.

FIGS. 5a and 5b indicates an example of the result of the study of the effect owing to the performance of this invention. The specimen was a net (500 meshes) made of nickel, which had a wire width of 16 μm. Experimental conditions were that $O_2^+$ ions at 10 keV were employed as the primary ions and that the beam diameter was set at 2 μm. As previously stated, FIGS. 3a and 3b indicate an example of the result of the analysis with the prior art apparatus. When the $Ni^+$ ion intensity in the case of fixing the ion beam on the wire as illustrated in FIG. 3a is set to be 1, the measured value in the case of fixing the beam at the place at which no wire existed, as illustrated in FIG. 3b, is about ¼. The ion intensity of ¼ signifies noise ascribable to the neutral particles.

FIGS. 5a and 5b illustrate the example of removing the influence of the neutral particles by the use of the embodiment of this invention. FIG. 5a corresponds to the case where the ion beam was projected onto the wire, and FIG. 5b the case where it was projected onto the place at which the wire did not exist. As indicated in FIG. 5b, no $Ni^+$ ion current was detected at the place deviating from the wire. It is accordingly understood that the undesirable influence by the neutral particles is fully eliminated by the present invention.

Further, using the neutral particle beam, the analysis of impurities in phosphorus glass, the analysis of sodium in mica, and the analyses of organic materials were performed. In these tests, analytical values of high precision were successfully obtained without evidence of the charge accumulation phenomenon.

Figure 6:
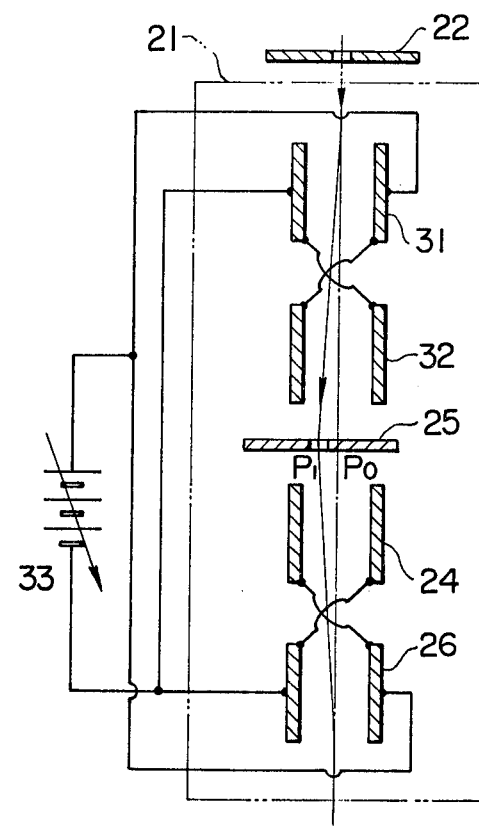
FIG. 6 is an explanatory schematic diagram of another embodiment of this invention.

FIG. 6 shows another embodiment of this invention. The deflecting means 21 in the figure is disposed on the primary ion beam optical axis and between, for example, the ion source 1 and the primary ion beam focusing system including the condenser lenses 2 and the subsequent components. The deflecting means 21 is composed of two pairs of first deflector electrodes 31 and 32, two pairs of second deflector electrodes 24 and 26, and a movable aperture 25. Shown at 33 is a power supply for applying electric potentials to the deflectors. In the present embodiment, the aperture 25 is movable, by way of example, in a beam deflecting direction perpendicular to the ion beam optical axis. Preferably, the deflector electrodes 31, 32, 24 and 26 are made of parallel plate electrodes of the same size. With such a construction, voltages of the same magnitude are applied to the four deflectors. The polarities of the voltages are the same for the deflectors 31 and 26, and the same for the deflectors 32 and 24. The voltages at such polarities are applied in an alternate manner. Then, the ion beam vertically entering from above emerges vertically at all times after passing through the deflecting system. Of course, even when the shapes of the deflectors are arbitrarily selected, the vertical emergence of the ion beam on the axis can be realized by applying proper voltages to the respective deflectors.

The aperture 25 is designed so as to be movable forwards and rearwards and rightwards and leftwards within a horizontal plane. The aperture 25 has the following two functions. First, the aperture 25 is arranged at a point $P_1$ deviating from the axis (point $P_O$) of the deflectors, as shown in FIG. 6, whereby the neutral particles are removed and the ion beam is deflected, as shown by the deflecting system, so as to reach the specimen. Secondly, the aperture 25 is arranged on the axis (the point $P_O$), whereby the neutral beam can reach the surface of the specimen, and simultaneously therewith, a proper voltage is applied to any one of the deflectors 31, 32, 24 and 26, whereby the ion beam is deflected so as to cause it to be intercepted, thereby preventing it from reaching the specimen surface.

According to such method, the ion beam and the neutral particles can be independently taken out by moving the aperture 25. Further, since the aperture is disposed at the intermediate point of the four pairs of deflector electrodes, the separation between the ion beam and the neutral beam can be made at the point of the greatest deviation from the ion beam optical axis, and hence, the separation is easy. Yet further, since the ion beam incident on the aperture 25 is perpendicular to the aperture, a good separation is possible. In addition, since the beam axes or paths are symmetric before and behind the aperture 25, the axial adjustment thereof is easy.

Figure 7A:
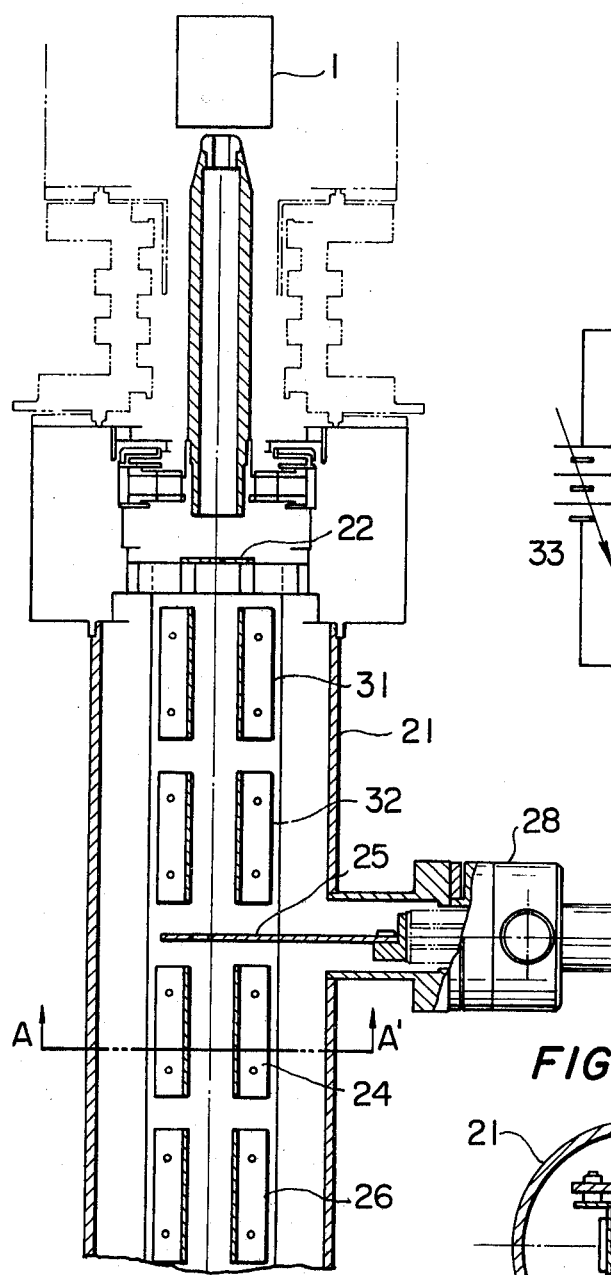
FIGS. 7a and 7b are schematic partial sectional views of still another embodiment of this invention.
Figure 7B:
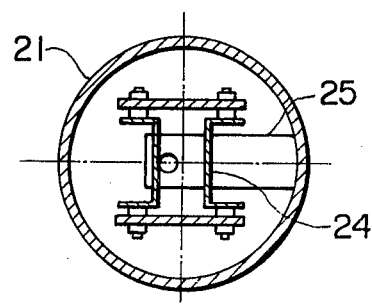

FIG. 7 is a detailed view of an example in which the aperture 25 in this invention is made movable. FIG. 7a is a sectional view along the ion beam optical axis, and FIG. 7b is a sectional view along line A-A' in FIG. 7a. Shown at 28 is means for moving the aperture 25. The stages succeeding the deflecting means 21 and the power supply means are omitted for the sake of simplicity.

From the comparison of measurements on a wire of a net made of nickel and at a part at which no wire existed, it has been shown that, similar to the foregoing embodiments, this embodiment eliminates the neutral particle beam. Also, in the analysis of impurities in phosphorus glass, etc., with the neutral particle beam, analytical values of high precision were obtained without evidence of the charge accumulation phenomenon.

The effects of this invention described above are summarized as below:

a. Owing to the removal of the neutral particle beam, high-precision analyses have become possible.

b. Analyses employing only the neutral particle beam have become possible, and the analyses of insulators have become possible.

c. It has become possible to separately use the ion beam and the neutral particle beam.

While we have shown and described several embodiments in accordance with the present invention, it is understood that the same is not limited thereto but is susceptible of numerous changes and modifications as known to a person skilled in the art, and we therefore do not wish to be limited to the details shown and described herein but intend to cover all such changes and modifications as are obvious to one of ordinary skill in the art.

What is claimed is:

1. In an ion microprobe analyzer wherein a specimen is irradiated by a primary ion beam derived from an ion source and projected along an optical axis by a primary ion focusing system, and wherein secondary ions generated from the specimen are analyzed, the improvement comprising ion beam deflecting means disposed between said ion source and said specimen, including:
  a. an aperture which is movable between a position on the ion beam optical axis and a position deviating from said optical axis;
  b. first deflector means for deflecting said ion beam towards the point where the aperture is situated when at the deviating position; and
  c. second deflector means for deflecting forwards along said ion beam optical axis the ion beam which passes through said aperture situated at said deviating position.

2. The ion microprobe analyzer according to claim 1, wherein said ion beam deflecting means is disposed between said ion source and said primary ion focusing system.

3. The ion microprobe analyzer according to claim 2, wherein a further aperture is disposed between said ion source and said ion beam deflecting means.

4. The ion microprobe analyzer according to claim 1, wherein said first deflector means is composed of two pairs of electrodes of the same size, and said second deflector means is composed of two pairs of electrodes of the same size as said first deflector electrodes.

5. The ion microprobe analyzer according to claim 4, wherein each of the four pairs of deflector electrodes consists of a pair of plate electrodes which are disposed on respective sides of said ion beam optical axis.

6. The ion microprobe analyzer according to claim 1, wherein said first deflector means is composed of one pair of deflector electrodes, said second deflector means is composed of one pair of deflector electrodes having the same size as that of the first pair of deflector electrodes and a second pair of deflector electrodes having a length double that of the first pair of deflector electrodes, said second pair of deflector electrodes being disposed so as to be closer to the movable aperture than the former pair of electrodes.

7. The ion microprobe analyzer according to claim 6, wherein each of said pairs of deflector electrodes consists of a pair of plate electrodes disposed on respective sides of said ion beam optical axis.

8. The ion microprobe analyzer according to claim 1, wherein said first and second deflector means have their positions fixed with respect to said ion beam optical axis, and said aperture is movable within a horizontal plane perpendicular to said ion beam optical axis.

9. The ion microprobe analyzer according to claim 1, wherein said ion beam deflecting means is movable within a horizontal plane perpendicular to said ion beam optical axis.

10. In an ion microprobe analyzer wherein a primary ion irradiation system is disposed on a rectilinear axis, a specimen is irradiated by a primary ion beam projected from an ion source by a primary ion focusing system and secondary ions generated from the specimen are analyzed, the improvement comprising ion beam deflecting means disposed between said ion source and said specimen, and including:
  a. an aperture which is movable between a position on said rectilinear axis and a position deviating from said axis,
  b. first deflector means which deflects said ion beam towards the position of the aperture when situated at the deviating position thereof, and
  c. second deflector means which deflect the ion beam forwards along said axis, the ion beam which has passed through said aperture situated at said deviating position.

11. The ion microprobe analyzer according to claim 10, wherein said ion beam deflecting means is disposed between said ion source and said primary ion focusing system.

12. The ion microprobe analyzer according to claim 11, wherein a further aperture is disposed between said ion source and said ion beam deflecting means.

13. The ion microprobe analyzer according to claim 10, wherein said first deflector means is composed of two pairs of electrodes of the same size, and said second deflector means is composed of two pairs of electrodes of the same size as that of said first deflector means.

14. The ion microprobe analyzer according to claim 13, wherein each of the four pairs of deflector electrodes consists of a pair of plate electrodes which are disposed on respective sides of said axis.

15. In an ion microprobe analyzer wherein a specimen is irradiated by a particle beam projected along an optical axis from an ion source which produces a beam consisting of both ions and neutral particles, and wherein secondary ions generated from the specimen are analyzed, the improvement comprising ion beam deflecting means disposed between said ion source and said specimen, including:
  a. an aperture plate having an aperture which is positioned on said optical axis; and
  b. first deflector means positioned upstream of said aperture plate for deflecting the ions projected from said ion source away from said optical axis so as to allow only said neutral particles to pass therethrough.

16. The ion microprobe analyzer according to claim 15, further including positioning means for selectively moving at least said aperture plate to a position where the aperture thereof is aligned with the path of the ions deflected by said first deflector means so as to pass said ions while blocking said neutral particles, and second deflector means for deflecting the ions passing said aperture plate back to a path coincident with said optical axis.

17. The ion microprobe analyzer according to claim 16, wherein said positioning means effects movement of said aperture plate with respect to said first and second deflector means transversely to said optical axis.

18. The ion microprobe analyzer according to claim 16, wherein said positioning means effects movement of said aperture plate as well as said first and second deflector means transversely with respect to said optical axis.

19. The ion microprobe analyzer according to claim 16, further including a primary ion focusing system for focusing said ion beam, said ion beam deflecting means being disposed between said ion source and said primary ion focusing system.

20. The ion microprobe analyzer according to claim 16, wherein said first deflector means is composed of one pair of deflector electrodes, said second deflector means is composed of one pair of deflector electrodes having the same size as that of the first pair of deflector electrodes and a second pair of deflector electrodes having a length double that of the first pair of deflector electrodes, said second pair of deflector electrodes being disposed so as to be closer to the movable aperture than the former pair of electrodes.

* * * * *